United States Patent
Kennedy et al.

(10) Patent No.: US 10,078,038 B2
(45) Date of Patent: Sep. 18, 2018

(54) CONTROLLED COALESCENCE OF GAS PHASE SEGMENTED DROPLETS

(71) Applicant: THE REGENTS OF THE UNIVERSITY OF MICHIGAN, Ann Arbor, MI (US)

(72) Inventors: Robert T. Kennedy, Ann Arbor, MI (US); Qiang Li, Saginaw, MI (US); Gary A. Valaskovic, Cambridge, MA (US); Claire Chisolm, Silver Spring, MD (US); Joanna E. Thielen, Ann Arbor, MI (US)

(73) Assignee: The Regents of The University of Michigan, Ann Arbor, MI (US)

(*) Notice: Subject to any disclaimer, the term of this patent is extended or adjusted under 35 U.S.C. 154(b) by 141 days.

(21) Appl. No.: 15/016,742

(22) Filed: Feb. 5, 2016

(65) Prior Publication Data
US 2016/0266017 A1    Sep. 15, 2016

Related U.S. Application Data

(60) Provisional application No. 62/112,955, filed on Feb. 6, 2015.

(51) Int. Cl.
*G01N 1/34* (2006.01)
*B01D 15/42* (2006.01)
(Continued)

(52) U.S. Cl.
CPC ............ *G01N 1/34* (2013.01); *B01D 15/163* (2013.01); *B01D 15/424* (2013.01); *G01N 30/32* (2013.01);
(Continued)

(58) Field of Classification Search
CPC ...... G01N 1/34; G01N 30/32; G01N 30/7233; G01N 2030/009; G01N 2030/326;
(Continued)

(56) References Cited

U.S. PATENT DOCUMENTS 8,431,888 B2    4/2013 Kennedy et al.
2011/0053798 A1    3/2011 Hindson et al.
(Continued)

FOREIGN PATENT DOCUMENTS

EP    1508044 B1    9/2010
WO    2008-142393 A1    11/2008
WO    2014-194272 A2    12/2014

OTHER PUBLICATIONS

International Search Report and Written Opinion of the International Searching Authority regarding International Application No. PCT/US2016/016807, dated May 20, 2016.

*Primary Examiner* — Daniel S Larkin
*Assistant Examiner* — Anthony W Megna Fuentes
(74) *Attorney, Agent, or Firm* — Harness, Dickey & Pierce, P.L.C.

(57) ABSTRACT

A one-dimensional linear array of liquid plugs separated by a gas phase is coalesced by (1) pumping the array through a conduit having a flow restriction of sufficient resistance or (2) a rapid and sudden increase in applied pressure (such as by increasing the flow rate). In this way, the flow of material through the conduit is restricted sufficiently to compress the gas phase into (partial or full) solubility within one or more components of the liquid phase.

20 Claims, 7 Drawing Sheets

(51) Int. Cl.
*B01D 15/16* (2006.01)
*H01J 49/16* (2006.01)
*G01N 30/32* (2006.01)
*G01N 30/00* (2006.01)
*G01N 30/72* (2006.01)
*G01N 30/02* (2006.01)
*H01J 49/04* (2006.01)

(52) U.S. Cl.
CPC ........ *G01N 30/7233* (2013.01); *H01J 49/165* (2013.01); *G01N 2030/009* (2013.01); *G01N 2030/027* (2013.01); *G01N 2030/326* (2013.01); *H01J 49/04* (2013.01)

(58) Field of Classification Search
CPC ............ G01N 2030/027; B01D 15/424; B01D 15/163; H01J 49/165; H01J 49/04
See application file for complete search history.

(56) References Cited

U.S. PATENT DOCUMENTS

2012/0153143 A1\* 6/2012 Kennedy ............... H01J 49/165
 250/282
2015/0174576 A1\* 6/2015 Van Vilet .............. B01L 3/0241
 506/12

\* cited by examiner

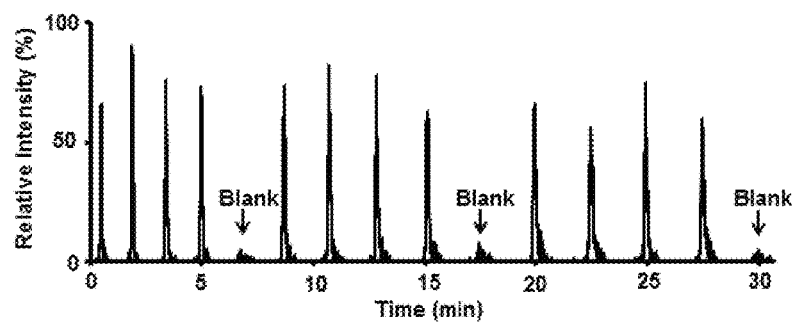
*FIG. 3A*
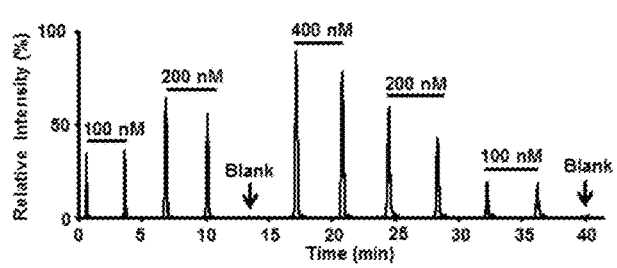 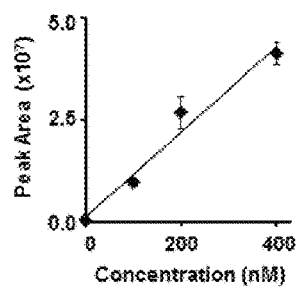
*FIG. 3B*  *FIG. 3C*

CONTROLLED COALESCENCE OF GAS PHASE SEGMENTED DROPLETS

CROSS-REFERENCE TO RELATED APPLICATIONS

This application claims the benefit of U.S. Provisional Application No. 62/112,955, filed on Feb. 6, 2015. The entire disclosure of the above application is incorporated herein by reference.

INTRODUCTION

Droplet-based microfluidics is an emerging method for manipulating low volume (picoliter to microliter) samples. Droplet methods have been developed for a variety of applications including high-throughput screening, in vivo monitoring, and protein crystallization. In such systems, samples are compartmentalized by air or an immiscible liquid that is confined within a channel or capillary. When droplets are large enough, they span the walls of the channel to form plugs that can be pumped as a series of samples with predetermined order, in so-called segmented flow. A variety of analytical operations can be performed on droplets including reagent addition, dilution and splitting. These methods enable analysis of complex mixtures at low volume and high throughput characteristic of droplets.

A limitation of using mass spectroscopy to analyze droplets is that components of many samples, such as salts and buffers, suppress signal and complicate the mass spectrum. For this reason, complex mixtures can be simplified before mass spectroscopy (such as by inductively coupled plasma mass spectrometry (ICP-MS), matrix-assisted laser desorption ionization (MALDI)-MS and electrospray ionization (ESI)-MS) by methods like solid-phase extraction (SPE) or HPLC. Methods are described in Kennedy et al., U.S. Pat. No. 8,431,888, the entire disclosure of which is useful for background information and is hereby incorporated by reference.

But even if the sample can be made MS-friendly by removing interfering components in this way, segmented flow with liquid plugs separated by a gaseous plug (e.g., air) introduces other complications into the separation and clean-up of samples being carried out by passing the individual plugs sequentially through the extraction bed or chromatography column. Despite the advances in the art, it has been observed that he presence of air "pockets" in the flow of materials being introduced to the chromatography column still tends to interfere with and slow down the desired separation and throughput of the column operating under segmented flow.

SUMMARY

New methods involve arrangements of droplets in a one-dimensional, linear array, with one or more portions of the droplet array separated by a gas phase; a form referred to here as segmented flow. In an innovation, such a linear array, or array segment—also known as one-dimensional linear array—is coalesced by (1) pumping the array through a conduit having a flow restriction of sufficient resistance or (2) a rapid, and sudden increase in applied pressure (such as by increasing the flow rate). In this way, the flow of material through the conduit is restricted sufficiently to compress the gas phase into (partial or full) solubility within one or more components of the liquid phase, or else into a sufficiently small bubble that no longer physically separates the droplet segments of interest within the conduit. While plugs within an array are intentionally coalesced in this way with a neighboring plug, multiple arrays can be separated by an incompressible, immiscible liquid phase to prevent coalescence between arrays.

For example the flow restriction can be an electrospray nozzle, providing that samples can be introduced sequentially, after coalescence, into an emitter tip for mass spectrometry analysis. In another example, the flow restriction is a solid-phase porous substrate disposed in the conduit to serve as a separation device such a solid phase extraction bed (SPE). In various embodiments, the porous substrate is in the form of, e.g., a packed bed of beads or a porous-bed monolith. In a particular application, the droplets before coalescence contain a series of samples, rinse, elution, and re-equilibration droplets that are coalesced before passing over the solid phase porous substrate to provide a sequence of washings without interference from gas phase plugs present between the liquid plugs. In this way, a sample or series of samples is extracted and eluted from the extraction bed. Interface of this system to a electrospray nozzle allows direct SPE-electrospray ionization (ESI)-mass spectrometry (MS) of the samples.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1A is a diagram of segmented droplet generation from a multiwell plate. As the syringe pump refilled at a constant rate, the inlet of the tubing is moved from well to well by a computer-controlled XYZ-positioner. The volume of the droplets and air or oil segments was controlled by the dwell time of the tubing inlet in or above the well.

FIG. 3A is an extracted ion chromatogram (XIC) of twelve air-segmented 35 nL 100 nM LE (for leu-enkephalin) samples extracted from artificial cerebral spinal fluid (aCSF). LE is detected by the following $MS^3$ pathway (m/z): 556→397→278, 323, 380. Carry-over is detected in the blank samples that were placed between the LE samples.

FIG. 3B is an XIC of ten air segmented 35 nL LE standards of varying concentration extracted from aCSF.

FIG. 3C is a diagram of a calibration curve of extracted LE standards. The peak area shows good linearity with respect to concentration ($R^2 > 0.97$).

Figure 4:
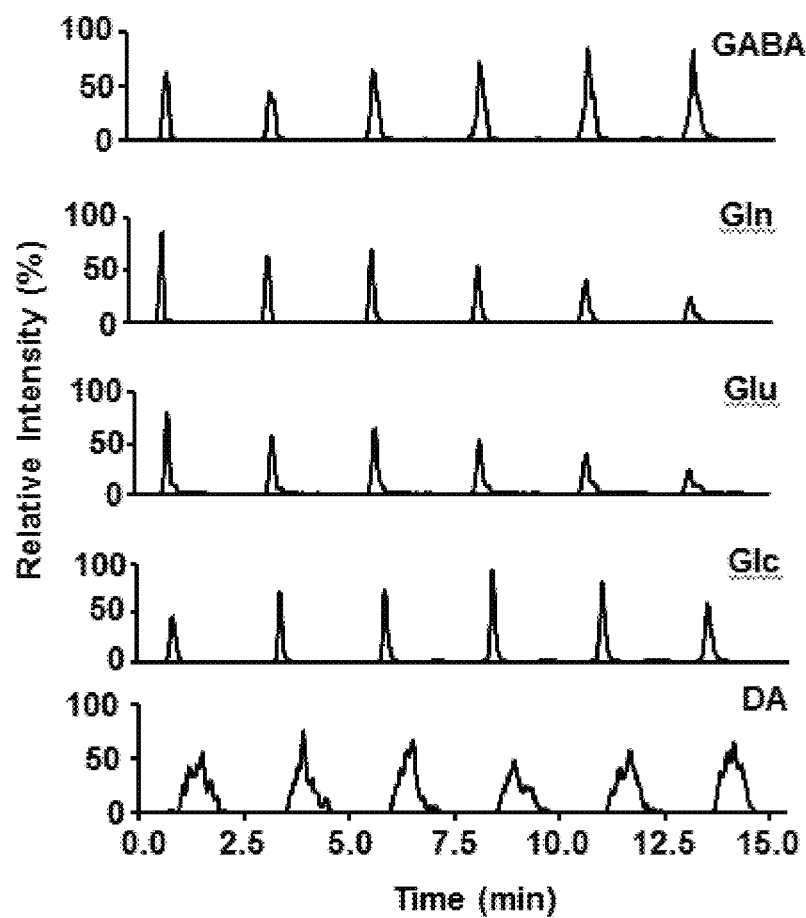

FIG. 4 is an XIC of five endogenous neurotransmitters and metabolites extracted from dialysate and detected by ESI-MS simultaneously. These analytes were detected by the following MS$^2$ pathways (m/z): 208→105 (GABA), 251→105 (Gln), 252→105 (Glu), 307→185 (Glc), 466→105 (DA).

Figure 5A:
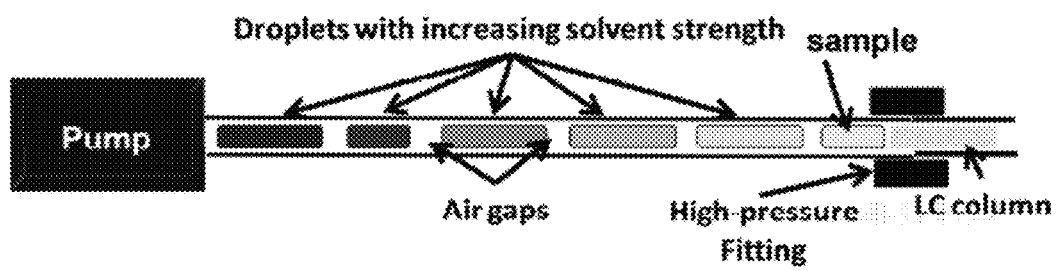
Figure 5B:
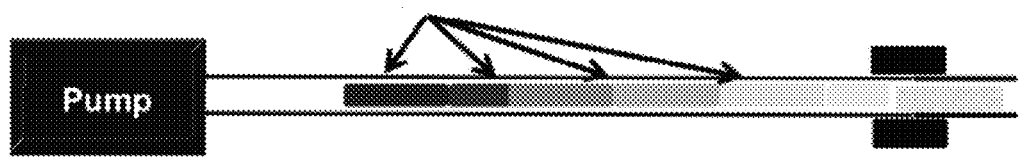

FIGS. 5A and 5B illustrate arrays of pre-formed droplets for gradient elution. In FIG. 5A, droplet arrays are formed in-line with a sample. In FIG. 5B, the droplets coalesce after pressurization to form a gradient of composition suitable for gradient elution H PLC.

Figure 6A:
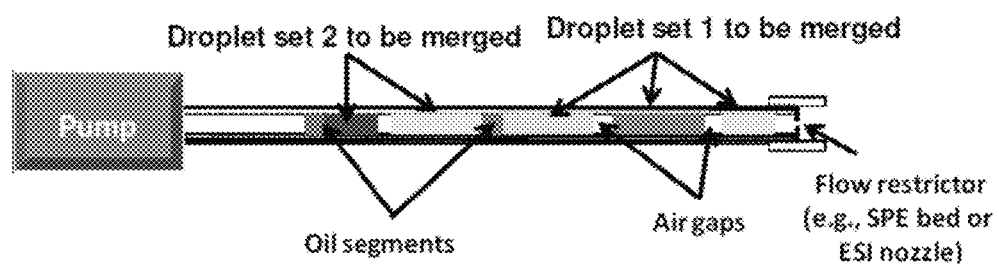
Figure 6B:
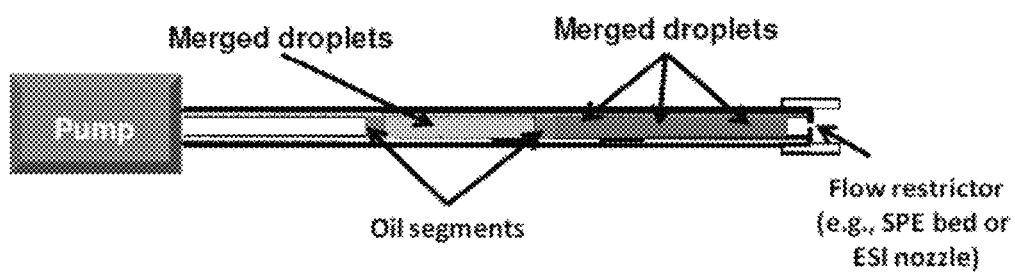

FIGS. 6A and 6B illustrate use of oil and air-segments to form arrays of droplets that will be merged or kept separate after pressurization. In FIG. 6A, prior to pressurization, all droplets are kept separate in the tube by either air or oil gaps. In FIG. 6B, air-segmented droplets coalesce after pressurization while oil segments keep different droplets separated.

Figure 7A:
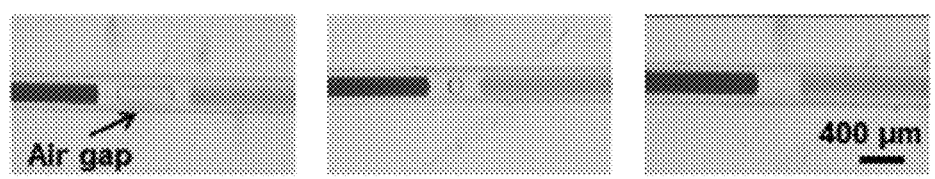

FIG. 7A shows photomicrographs of oil segments before infusion (left), during infusion (middle, air segment has compressed to approximately a third of its original size) and after infusion (right, air segment has been completely compressed).

Figure 7B:
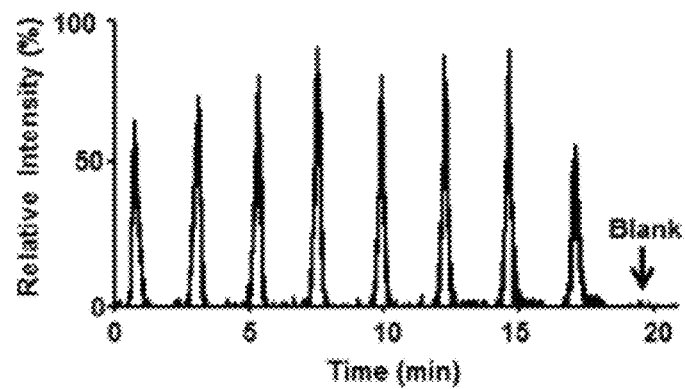

FIG. 7B shows XIC of eight oil-segmented 35 nL 100 nM LE samples extracted from aCSF. Carry-over was 0.4%.

Corresponding reference numerals indicate corresponding parts throughout the several views of the drawings.

DETAILED DESCRIPTION

In one embodiment, a method involves providing a one-dimensional linear array of liquid plugs in a conduit, wherein the array contains two adjacent liquid plugs separated by a gas phase plug. A pressure is applied to the proximal end of the conduit to advance the linear array in a flow path toward a restriction in the conduit. Sufficient pressure is applied to the proximal end of the conduit to cause the two adjacent plugs in the array to coalesce into a single plug, and the coalesced single plug is advanced through the restriction. The conduit provides the flow path for the one-dimensional linear array. It has a continuous, closed-form inner surface and has an opening at the proximal and distal ends of the conduit. Furthermore, the conduit contains a restriction continuous with the inner surface and located at the distal end of the conduit. The restriction contains a solid phase porous substrate. In various embodiments, the solid phase porous substrate is exemplified as a packed particle bed, as a porous phase coated on the interior walls of the conduit, or as a porous monolith. Operationally, the restriction involves a solid phase porous substrate that in non-limiting fashion is in the form of a liquid chromatography column or a solid phase extraction bed.

In a particular embodiment, adjacent liquid plugs in the one-dimensional linear array of liquid plugs have different concentrations of a solute such that the resulting coalesced plug comprises a concentration gradient of the solute along the length of the conduit. While the one-dimensional linear array has at least two adjacent plugs, the conduit can contain a plurality of arrays that are separated in the conduit by spacer plugs. Advantageously, the spacer plugs contain a solvent that is immiscible with a solvent found in the liquid plugs of the one-dimensional linear array. As used here, solvents are immiscible if they do not form a homogeneous mixture when added together.

For example, adjacent liquid plugs contain water, a water soluble organic solvent, or a combination. The spacer plugs can contain a perfluorocarbon liquid that is immiscible with the water and organic solvent.

In various embodiments, adjacent liquid plugs in the one-dimensional linear array contain reagents that react with one another when the contents of the adjacent plugs are mixed during coalescence. In another embodiment, at least one of the adjacent liquid plugs that is coalesced contains a solute that is diluted when the adjacent plugs coalesce under pressure. Although coalescence is described in terms of the coalescence of at least one pair of adjacent liquid plugs, it is to be understood that the one-dimensional linear arrays used in the methods can contain more than two liquid plugs, any number of which can be coalesced together when pressure is applied.

In another embodiment, a method involves forming a one-dimensional linear array in a conduit by aspirating a plurality of liquids in a desired order into a tube having a diameter sized such that the aspirated liquids form plugs that span the inner diameter of the tube and the plugs are separated from one another by a gas phase plug aspirated between the aspirated liquids. As in other embodiments, pressure is then applied to the linear array to coalesce at least two adjacent plugs in the conduit or tube. Thereafter, the coalesced plugs are advanced along the tube to pass through a separation device, which generally comprises a solid phase porous substrate as discussed above. In various embodiments, the separation device is configured as a chromatography column or as a solid phase extraction bed. In these and other embodiments, the output of the separation device can be provided to a mass spectrometer or to an electrospray ionization emitter nozzle coupled to a mass spectrometer.

In various aspects of these embodiments, aspirating is performed using a first pump and the advancing of the linear array through the conduit or tube is performed with a second pump. The first and second pumps can be the same or different.

As before, the one-dimensional linear array in some embodiments comprises a plurality of plugs that contain different levels of the same solute. As a result, when adjacent plugs are coalesced into a single plug, the resulting coalesced plug has a gradient of solute concentration along the conduit or tube.

In a particular embodiment, a method involves aspirating a sample droplet, a rinse droplet, an elution droplet, and second rinse droplet into a tube or conduit to make a segmented array, after which pressure is applied to the segmented array to coalesce the droplets. The coalesced droplets are then pumped in order through a separation device that is disposed in the tube as in the embodiments described above. The sample droplet deposits a sample on the substrate, while the rinse droplet washes un-retained components out of the substrate. The elution droplet then elutes the sample from the substrate and the second rinse droplet reconditions the porous substrate of the separation device.

In various embodiments, at least one of the liquid plugs in the one-dimensional arrays described herein contain a sample of biological origin. Non-limiting sample materials include blood, plasma, serum, urine, saliva, tears, spinal fluid, lavage fluid, bile, liquid homogenized tissue, dialysates of any of these fluids, or partially or completely purified fractions of these fluids of biological origin. Without limitation, the chemical species in the samples of biological origin include proteins, nucleotides, sugars, small molecules, and the like.

In an aspect of the invention, reference is made to the system for electrospray ionization of discrete samples described in U.S. Pat. No. 8,431,888. Applicants incorporate by reference the figures and descriptions of U.S. Pat. No. 8,431,888 as it relates to pumping of one-dimensional segmented sample arrays through a tube or conduit towards a restriction such as a chromatography column, solid phase extraction column, and the like, optionally as input to an electrospray emitter nozzle as input to a mass spectrometer. An improvement over the system and methods disclosed in U.S. Pat. No. 8,431,888 involves the application of pressure at a fortuitous time in segmented flow to coalesce adjacent liquid plugs in the one-dimensional linear array in order to provide the advantages described herein.

Embodiments of the invention are described herein, reciting certain values for some of the limitations and certain examples or alternatives for some of the components of the invention. It is to be understood that unless provided otherwise, each component of the invention can take on values described for any of the embodiments described herein. Several aspects of the embodiments will now be described in turn. It is understood that other embodiments can be described by combining any aspects of the separate limitations into a new embodiment.

Conduit

The conduit provides a flow path for the one-dimensional linear array of fluid plugs described herein. A conduit is intended to be a generic designation, indicating that the flow path is a closed flow path so that the conduit will hold pressure when it is applied to coalesce adjacent plugs. For this reason, the conduit is said to be closed-form, as opposed to an open channel, which would also be a conduit for fluids, but would not take pressure to coalesce droplets. One form of a conduit is a tube, such as a tube fabricated from silicone, fluorinated-ethylene-propylene co-polymer (FEP), or the like that has an opening at two ends—one of which is called proximal and the other of which is called distal. Preferably the closed form of the conduit has a shape having a circular cross section, with the resulting inner bore of the conduit having the approximate geometry as a cylinder. Other suitable materials for conduit fabrication include, but are not limited to, metals such as stainless steel, nickel, and nickel-chromium alloys; glass ceramics, such as fused-silica or borosilicate glass; and other polymers including polyethylene, polypropylene, poly-etheretherketone (PEEK), polyethylene terephthalate (PET), poly-ether-imide, poly-dimethylsiloxane (PDMS), perfluoroalkoxy alkane (PFA), and polytetrafluoroethylene (PTFE).

Although "conduit" is a generic term, the conduit can take on various physical forms, including tubes as just discussed and including microfluidic pathways through solid substrates. Examples of conduits are provided in the working examples.

The conduit is sized so that the liquid plugs aspirated into the conduit preferably span the walls and form plugs. Advantageously, the liquid plugs can be on the picoliter to microliter scale, which means that the conduit has a relatively small diameter. In various embodiments, the conduit is one millimeter or less, 0.5 millimeters or less, 150 microns or less, or about 20 to 100 microns in diameter, where diameter refers to the inner diameter of the conduit. In various embodiments, it is preferable to choose the inner diameter of the conduit such that the meniscus surface of a liquid plug of given volume forms a continuous convex or concave shape, which adds stability to the integrity of the plug as it moves through the conduit. Suitable sizes and volumes are given in the examples.

Restriction in the Conduit

A restriction is provided in the distal end of the conduit. A restriction is applied in the conduit at the distal end so that when pressure is applied from the proximal end, the pressure forces adjacent liquid plugs to coalesce.

In one aspect, the restriction is supplied by providing a solid phase porous substrate that is continuous with the inner surface of the conduit. In one aspect, the solid phase porous substrate takes the form of a packed particle bed retained within the conduit by a screen, frit, filter, or other fluid-passing and particle-retaining element integrated into the body of the conduit. By way of reference, suitable methods for the fabrication and deployment of such frits within a conduit are taught in US patents to Ford U.S. Pat. No. 5,911,954; Yang U.S. Pat. No. 4,483,773; or Cortes U.S. Pat. No. 4,793,920), the full disclosures of which are incorporated by reference. In non-limiting fashion, such can be provided by silica particles having a diameter of ≤20 microns, ≤5 microns, or ≤3 microns. The particles are preferably those used in the chemical separation of mixtures, known to those skilled in the art of liquid chromatography. Particularly preferred are spherically shaped porous, or semi-porous particles, made from ultra-pure silica, and chemically derivatized on their surface, to specifically adsorb desired chemical components present in the liquid plugs. Particles are preferably suitable for use in one or more of the many modes of liquid chromatography and chemical separations known to those skilled in the art, including, but not limited to, reverse phase, normal phase, ion exchange, hydrophobic interaction, affinity binding, and ion-pairing chromatography. In another aspect, the solid phase porous substrate is provided as a thick polymer porous phase coated on the inner walls of the conduit. Such a coating would need to be thick enough to restrict the inner diameter of the conduit by 25% or more. By way of reference, a suitable polymer coating has been taught in U.S. Pat. No. 8,580,570 to Karger et. al., incorporated herein by reference. In other aspects, the solid phase porous substrate is a porous polymer monolith. Non-limiting examples of polymer monolith are disclosed in U.S. Pat. No. 8,691,088 to Karger et. al and U.S. Pat. No. 5,316,680 to Frechet et. al. These materials are provided as a restriction in the conduit. Upon applying conditions to the conduit containing the restrictions, the pressure can be increased locally so that the adjacent plugs are coalesced, as described further herein.

In addition to providing a physical restriction to allow for pressure increase by, for example, increasing a flow rate, the solid phase porous substrates can provide various chemical separation devices such as chromatography columns and solid phase extraction columns. Without limitation, the solid phase porous substrates can be derivatized to provide chromatography columns, affinity ligand columns ion exchange columns, and the like. Because of their derivatization and use as chromatography columns and solid phase extraction beds, the restrictions in this form are also referred to as separation devices Adjacent Plugs The liquid plugs of the one-dimensional linear arrays formed in the conduits, according to these teachings, are separated by a gas phase plug. The liquid plugs on either side of a gas phase plug are referred to as adjacent plugs or adjacent liquid plugs. Because the gas phase plug is compressible, the adjacent liquid plugs can coalesce when a pressure is supplied. The liquid plugs generally contain solvent and a solute. The solvent in various embodiments is aqueous, containing either water by itself or water in combination with various water soluble organic solvents. As noted, the adjacent liquid plugs advance in the linear array as individual plugs separated by a gas phase until pressure is applied to coalesce the adjacent plugs.

Applying Pressure

It has been found that linear arrays or array segments can be reliably coalesced by (1) pumping the array through a conduit having a flow restriction of sufficient resistance or by (2) a rapid and sudden increase in applied pressure such that the flow of material through the conduit is restricted sufficiently to compress the gas phase into partial or full solubility within one or more components of the liquid phase in the adjacent liquid plugs. One way of increasing the pressure is to increase the pumped flow rate at the proximal end of the conduit towards and through the restriction provided in the conduit. As the flow rate at the proximal end increases, the resistance generated by the restriction causes the pressure on the gas phase to increase. The increase in pressure results in a reduction in gas volume. When the pressure is sufficiently high, and the gas phase is compressed to a diameter smaller than that of the conduit bore, and the adjoining liquid drops will coalesce providing they are miscible. The pressure on the proximal end of the conduit may be increased by a number of other suitable means. These include the application of high liquid or gas pressure from a source such as a piston style pump, a syringe style pump, or a static source of high pressure such as bottled gas. The pressure required to cause coalescence of adjacent liquid plugs is dependent on the diameter of the conduit, the length of the gas space, and the porosity of the restriction. Applied pressures in the range of 100 to 1,000 pounds per square inch (PSI) are typically sufficient to cause coalescence.

Coalescence

When pressure is applied, the compressible air plug between two adjacent liquid plugs responds by changing its volume. As the volume decreases under the applied pressure, at a certain point the bubble provided by the gas phase plug is no longer able to span the conduit. As a result, two adjacent liquid plugs are joined or coalesced. As further pressure is applied, the gas bubble that used to be the air plug between the liquid plugs can even be seen to disappear, as some of the gas is dissolved into the surrounding materials. Although the invention does not rely on theory, it is believed that the gases in the air plugs can be dissolved in the adjacent liquid plugs, in the tubing, or in a fluorocarbon solvent such as perfluorodecalin that is used to separate the arrays.

It is to be appreciated that coalescence during the segmented flow can be timed to provide a desired result. If coalescence results in a long plug having a gradient concentration, it can be desirable to use the coalescent plug almost immediately after coalescence so that the concentration gradient can be sustained. Likewise, when sequential sample, rinse, elution, and rinse plugs are part of the one-dimensional linear array, it can be desirable to coalesce the plugs at the last minute so that the sequential deposit, rinsing, elution, and reconditioning of the column can be carried out. Alternatively, under some conditions it may be desirable to coalesce the drops and use them later. This could be the case when reagents in adjacent liquid plugs are designed to react once the plugs coalesce.

Advancing the Array

The arrays can be advanced toward the distal end of the conduit in any suitable way. In various embodiments, pumps, vacuum, and aspiration can provide the force for advancing the linear arrays. Pumping means used for directing and manipulating the one-dimensional linear array of liquid plugs can be any suitable method for generating a desired flow rate. These include use of mechanical devices such as syringe pumps, reciprocating piston pumps, or peristaltic pumps. Gas-pressure, electroosmosis, and gravity can also be used for advancing the arrays. In one configuration, a pump is used to aspirate plugs into the conduit in the form of arrays, and the same pump is used to advance the arrays from the distal end to the proximal end toward a restriction, as described. In other embodiments, a first pump can be used to aspirate the liquid plugs in the form of a one-dimensional linear array and the conduit stored until it can be taken to a second pump that will advance the arrays into a restriction and for further analysis, such as into a mass spectrometer. In this way, analyses can be carried out and use can be made of specialized equipment such as the mass spectrometer, even if it is not in the same laboratory where the one-dimensional linear arrays are made.

Separation Devices

Separation devices can be installed in the conduit to provide both the restriction needed to control pressure and to provide for separation and analysis of samples. In various embodiments, the separation devices are in the form of a solid phase extraction bed, a liquid chromatography column, an ion exchange column, an affinity chromatography column, and the like. This general scheme also works for other modes of liquid chromatographic separation known to those skilled in the art. These include normal phase chromatography, hydrophobic interaction chromatography, affinity (ligand-substrate) chromatography, chiral chromatography, ion-exchange chromatography, and metal affinity chromatography.

In a particular application, a series of sample plugs, rinse plugs, and elution plugs are coalesced to remove air bubbles between the plugs. The sample plug contains an analyte (such as a protein, peptide, metabolite, organic drug, etc.) and is pushed through and retained by a suitable chromatographic bed (C18 based silica material, by way of example) that is disposed in the distal end of the conduit. The next liquid plug of highly aqueous (greater than 90 percent water) composition, washes the retained sample of non-retained and interfering species such as inorganic cations and anions. A subsequent plug or plugs is composed of an aqueous/organic co-solvent such as methanol or acetonitrile suitable to cause the retained analyte to elute from the chromatographic bed. Such elution could be conducted with a single plug of relatively high co-solvent composition (greater than 50 percent organic) or it could be eluted with a plurality of single plugs that are coalesced before passing through the chromatographic bed. The result is a one-step solid phase extraction of retained analytes.

Alternatively, a number of segments n, (where n can be 2 to about 100 or more) can be used to emulate gradient elution chromatography. In this case, each succeeding plug would be of organic/aqueous composition having a higher percent composition of co-solvent, generating a discrete step elution from the column.

Spacer Plugs

If desired, the one-dimensional linear array of liquid plugs contains a plurality of individual arrays. Advantageously, the arrays can be separated from one another using an solvent that is immiscible with the liquid phase of the liquid plugs. In various embodiments, it is preferred to use a fluorocarbon solvent such as perfluorodecalin to separate the individual arrays. Perfluorodecalin readily solubilizes oxygen and can act as a sink when air is compressed and begins to dissolve in various materials in the vicinity. The high solubility of oxygen in a solvent like perfluorodecalin can also contribute to maintaining a one-phase system of the coalesced liquid plugs, in that degassing can be avoided when the coalesced plugs travel over a pressure drop such as one supplied by the separation device in the conduit.

Advantages of Coalesced Droplets

When adjacent liquid plugs are separated by a gas phase plug and advance toward a separation device, the separation device disposed in the conduit sees first the first liquid plug, followed by an air gap, followed by a second liquid plug, a second air gap, and so on. The heterogeneous nature of these phases as they pass over and through the solid phase porous substrate in the conduit can lead to difficulties in flow and separation. Unless the system is highly optimized, for example, the air plugs passing through the separation device can lead to flow problems, causing poor separations, sample retention between plugs, and the like. In contrast, the current teachings permit taking advantage of the flexibility of analyzing one dimensional linear arrays of liquid plugs at the nanoliter or picoliter scale and avoiding the drawbacks of air plugs going through the separation devices.

Compositions of Adjacent Plugs

Depending on the application, the adjacent plugs can take on a variety of compositions. In one aspect, adjacent plugs can contain reagents that react with one another upon coalescence. The timing of coalescence of the droplets can be adjusted according to how long it is desired for the reagents to react before passing through another device such as a separation device. In another aspect, adjacent plugs can have differing concentrations of a solute such that upon coalescence, the coalesced plug has a concentration of solute intermediate between that of the two adjacent plugs.

Forming One Dimensional Arrays of Liquid Plugs

Adjacent plugs are formed with a gas phase plug in between them. One way of forming the one-dimensional linear array of liquid plugs is to aspirate plugs, for example, from a multi-well plate. A tip of an input device into a pump is dipped into one of the wells in a plate and the tip is then removed from that well and moved to another well. In various embodiments, the movement of the tip is under control of an X-Y-Z positioner. The rate of flow of the pump and the time of immersion in the particular well of the multi-well plate determines the size of the liquid plug. In advantageous embodiments, the volume of the liquid plugs is in the picoliter or nanoliter scale. Likewise, the size of the air plug between adjacent liquid plugs is determined by the amount of time it takes to move the tip from one well to another, in combination with the pumping speed. In this way, interaction of adjacent liquid plugs is avoided or put off until a later time at which a pressure is applied to coalesce adjacent plugs. Depending on the application, the coalesced drops are then immediately provided to a separation device or, in the alternative, are subject to a delay while the coalesced drops are advanced to the separation device. As noted, an advantage of the coalescence is to avoid air bubbles going through and over the solid phase porous substrate of the restriction provided in the conduit.

Various aspects of the invention have been described with regard to preferred embodiments. Further non-limiting description of the invention is given in the examples that follow.

EXAMPLES

Example 1

All chemicals and reagents were purchased from Sigma-Aldrich (St. Louis, Mo.) unless otherwise specified. Leu-enkephalin (LE) was purchased from American Peptide (Sunnyvale, Calif.). HPLC grade water, methanol (MeOH) and acetonitrile (ACN) were from Burdick & Jackson (Muskegon, Mich.). Acetic acid was from Acros Organics (New Jersey). Fused silica capillary was from Polymicro Technologies (Phoenix, Ariz.). Artificial cerebral spinal fluid (aCSF) contained 145 mM NaCl, 2.68 mM KCl, 1.0 mM $MgSO_4.7H_2O$, 1.40 mM $CaCl_2$, 1.55 mM $Na_2HPO_4$, and 0.45 mM $NaH_2PO_4.H2O$ adjusted to pH 7.4 (all salts purchased from Fisher Scientific, Pittsburgh, Pa.). LC-MS grade formic acid was purchased from Fisher Scientific (Pittsburgh, Pa.). Perfluorodecalin (PFD) was purchased from Acros Organics (New Jersey).

Figure 1A:
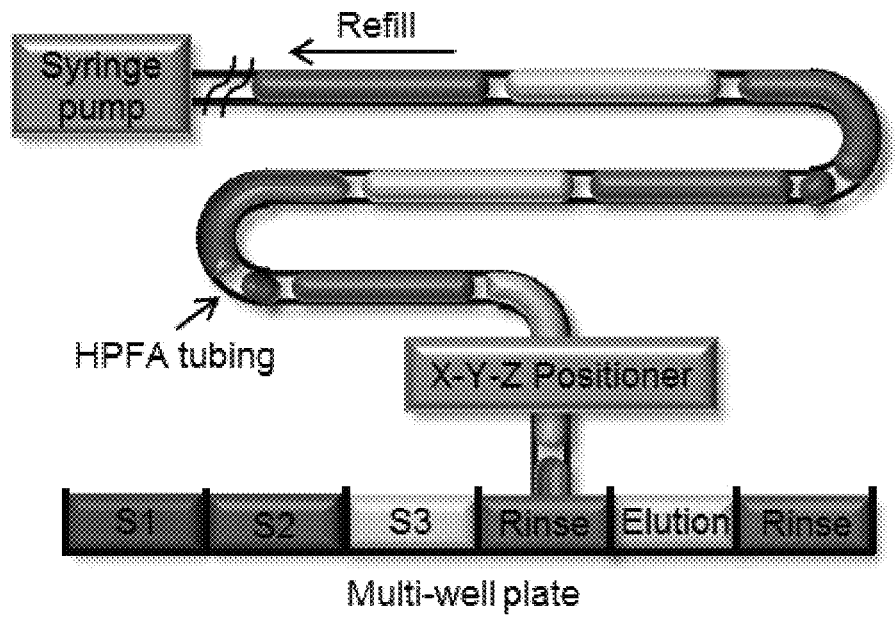
FIG. 1B is a diagram of droplet infusion and extraction. The syringe pump infused the droplets through the SPE packed bed and the Pt-coated emitter tip.

1.2 Sample Preparation and Analysis 1.2.1 Droplet Generation from a Multi-well Plate To perform SPE-ESI-MS, plugs of sample, rinse solvent, and elution solvent segmented by air, were aspirated in the desired order into a 150 µm i.d.×360 µm o.d. high purity "plus" perfluoro alkoxy alkane (HPFA) tube (IDEX Health and Science, Oak Harbor, Wash.) as illustrated in FIG. 1A. Droplets were aspirated at 800 nL/min from a 384 multi-well plate (MWP) using a syringe pump (Harvard Apparatus, Holliston, Mass.) as described before [S. Sun, T. R. Slaney, R. T. Kennedy, Analytical Chemistry 84 (2012) 5794, J. Pei, Q. Li, M. S. Lee, G. A. Valaskovic, R. T. Kennedy, Analytical Chemistry 81 (2009) 6558].

Figure 2A:
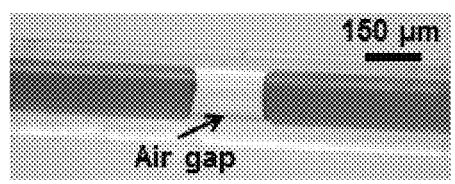
FIG. 2A is a photomicrograph of air segmented droplets after generation. Food dye was added to the droplets to facilitate visualization.

The volume of the droplets was controlled by the dwell time of the tubing inlet in the sample well. The HPFA tubing was prefilled with PFD oil which yields reproducible droplet size (i.e., as opposed to filling an empty tube where air expansion tends to cause droplet size to vary). Pre-filling with PFD also leaves a coating on the wall and results in the aqueous droplets showing a convex meniscus (FIG. 2A), indicative of little wetting of the tubing walls and promoting low carryover.

For tests using LE as the analyte, the rinse droplet was 450 nL of 5% MeOH and 2% acetic acid, the elution droplet was 450 nL of 60% MeOH and 2% acetic acid, the sample droplet was 35 nL of 100 nM LE in aCSF. The air segments were ~15 nL.

1.2.2 SPE-ESI-MS Analysis of Droplets

For SPE, a reversed-phase packed bed was prepared in-house using procedures similar to those previously described [Y. Zhou, O. S. Mabrouk, R. T. Kennedy, Journal of the American Society for Mass Spectrometry 24 (2013) 1700]. Silica sol-gel frits were made in the outlet of a 75 µm i.d.×360 µm o.d. fused silica capillary. The column was packed to 2 mm total bed length using a slurry of 10 µm Altima C18 reversed phase particles (5 mg/mL particles in 75% acetone, Grace Davison, Deerfield, Ill.) at 200 psi. The inlet end of the capillary was cut to reduce the total capillary length to 2 cm. The outlet of the SPE packed bed was connected to a 75 µm i.d. Pt-coated fused silica electrospray emitter tip that had a 30 µm i.d. tip (FS-360-75-30-CE, New Objective, Woburn, Mass.). The tubing containing droplets was connected to the inlet end of the packed bed capillary. Connections were made by inserting the two capillaries into either end of a short length of polytetrafluoroethylene (PTFE) tubing (1/16" o.d., 0.010" i.d., Grace Davison, Deerfield, Ill.) that fit snugly over the capillaries so that the capillaries were butted against each other.

For analysis, droplets were pumped through the SPE packed bed at 500 nL/min (FIG. 1B) using a syringe pump (Fusion 400, Chemyx, Stafford, Tex.). The emitter tip was interfaced to a LCQ Deca XP Plus quadrupole ion trap MS (Thermo Fisher Scientific, Waltham, Mass.) operating in positive mode with a nanospray ionization source assembled in-house. LE was detected by $MS^3$ using the following m/z pathway: 556→397→278, 323, 380. The following MS parameters were used for detection of LE: automatic gain control (AGC) on, collisional induced dissociation (CID) q=0.25, isolation width m/z 3 (for parent and daughter ion) and m/z 1 (for granddaughter ions), collision gas=He, normalized collision energies=30%, activation time=0.25 ms, number of micro scans=1, maximum injection time=400 ms, spray voltage=+17 kV, capillary voltage=41 V and capillary temperature=100° C. Extracted ion currents (XICs) of assay components were used for analysis. Peak detection was performed using Xcalibur Qual Browser (Version 2.0, Thermo Electron Co.).

1.2.3 Dialysate Collection and MS Analysis

Microdialysis probes (1 mm dialyzing length) were implanted in the nucleus accumbens of male Sprague-Dawley rats weighing between 300-350 g under isoflurane anesthesia. Procedures were similar to that previously described [42]. The flow rate was 1 µL/min and samples were collected every 10 min. Samples were derivatized with benzoyl chloride as described elsewhere [P. Song, O. S. Mabrouk, N. D. Hershey, R. T. Kennedy, Analytical Chemistry 84 (2012) 412]. Collected fractions were added to a MWP and droplets were generated as described above. For dialysate assay, the rinse droplet was 10 mM ammonium formate and 0.15% formic acid, the elution droplet was 30:70 10 mM ammonium formate and 0.15% formic acid:ACN and 0.15% formic acid. The blank droplet was 250 µM ascorbic acid in aCSF.

SPE-ESI-MS analysis of the dialysate droplets was performed as described above; but, using a triple quadrupole MS (TSQ Quantum, Thermo Fisher Scientific, Waltham, Mass.) operated in multiple reaction monitoring mode for detection. Five analytes were monitored using the following m/z pathways: 251→105 for glutamine (Gln), 307→185 for glucose (Glc), 466→105 for dopamine (DA), 252→105 for glutamate (Glu) and 208→105 for γ-aminobutyric acid (GABA). For all dialysate experiments, the following MS conditions were used: spray voltage=2 kV, capillary temperature=100° C., collision gas=$N_2$, scan width m/z 2, scan time=0.150 s, collision energy=25 eV, number of microscans=1, Q1 peak width=0.70 and Q3 peak width=0.3.

1.3. Results and Discussion 1.3.1 Demonstration of SPE-ESI-MS from Droplets

Initial experiments used 35 nL samples of LE dissolved in aCSF to test analysis at the nanoliter scale. The plugs were loaded into a tube such that during infusion, a sample droplet was first infused through the packed bed, retaining LE (FIG. 1). Next, a rinse droplet containing 5% MeOH flushed salts and other unretained chemicals from the packed bed. Then an elution droplet (containing 60% MeOH) eluted the retained LE. Finally another rinse droplet re-equilibrated the packed bed. Thus, the entire sequence of a normal SPE is encoded in the pre-formed droplet array so that the procedure can be performed without requirement of valves or binary solvent pumps.

As each elution plug emerged from the tip, a peak for LE was detected (FIG. 3A). Considering that LE could not be detected under these conditions without the SPE due to ion suppression, this result suggests effective desalting of the sample. For the sequence illustrated in FIG. 3A, blank samples containing only aCSF were interspersed after every four samples. The blank droplets after each four LE samples show that carryover is 7±1% (n=4). Detection of 100 nM LE was reproducible with a peak area RSD of 11%. The variability may be due to inconsistency in sample generation, extraction efficiency or MS detection.

The use of segmented flow allows calibration to be incorporated into a sequence. FIG. 3B illustrates a trace from a series of droplets with LE concentration from 100 to 400 nM and the resulting calibration curve ($R^2$>0.97). Based on these data, the limit of detection (LOD) was 10 nM, corresponding to 350 amol LE. The mass LOD is higher than we previously achieved for LE on this mass spectrometer (~1 amol) [43]; however, the goal of the experiments was not to test the limits of sensitivity and the instrument was not tuned for the peptide so considerable improvements may be attained by more care. As discussed below, better LODs can be obtained with proper tuning.

Pumping the sample array at 500 nL/min allowed generation of an SPE-ESI-MS analysis every 2.5 min (FIG. 3). This throughput is reasonable and could be improved by use of higher flow rates; however, the flow rate in the present system was limited by the low pressure tolerance of connections used to join different pieces of tubing.

Figure 2B:
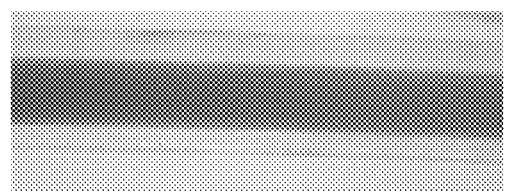
FIG. 2B is a photomicrograph of air segmented droplets after being pressurized for extraction and elution. During droplet infusion, the air segments compressed causing droplet coalescence.

Under the pressure of infusion the air segments compress resulting in coalescence of adjacent droplets (FIG. 2B). As a result, the different droplets begin to merge as they are transported to the packed bed and emitter. It is possible that mixing contributed to the carry-over that was observed. Any such mixing did not result in especially broad peaks as shown in FIG. 3A. This is likely because the gradient remains fairly sharp and reaches a concentration of organic solvent high enough to elute the test peptide over a short length of tubing.

1.3.2 Extracting Endogenous Neurotransmitters and Metabolites from Dialysate

To illustrate use of segmented flow SPE-ESI-MS for analysis of complex samples, we detected endogenous neurochemicals in dialysate collected from rat brain in vivo. Dialysate samples have a high concentration of inorganic salts and other compounds, which causes ion suppression effects in ESI-MS; therefore separation or extraction is required for analysis.

Infusing a series of samples with the elution and rinse droplets allowed extraction and simultaneous detection of five endogenous chemicals (the neurotransmitters GABA, Glu, and DA and the metabolites Gln and Glc) in dialysate samples at 2.5 min intervals (FIG. 4). Overall the peak shape was satisfactory. DA is triply labeled with the benzoyl moiety, making it very hydrophobic so it is highly retained on the reversed phase packed bed. As a result, the elution solvent used (70% ACN) may not be strong enough to elute DA in a band as sharp as the other analytes. We also found that during a sequence of replicates, the peak area for later replicates could decrease (e.g., Gln and Glu in FIG. 5). Larger peak areas could be regenerated by rinsing the column with 100% ACN, suggesting that longer rinse cycles may be necessary for a large sample set of complex samples.

By comparing peak areas to a calibration curve we were able to estimate the concentration in dialysate as follows: GABA=55±15 nM, Gln=6.0±0.6 µM, Glu=580±104 nM, Glc=81±34 µM, and DA=2.7±0.2 nM (n=8 except for DA and Gln which had one point that was determined to be an outlier at 95% confidence by Grubb's test). The determined concentrations are within expected values for dialysate under these conditions. All calibrations used 3 concentrations of analyte assayed in duplicate and had $R^2$>0.99. Reproducibility of standards was comparable to that observed for LE (7-12%); therefore, the variability observed in dialysate likely reflects the effects of subject variability or sample complexity. The result shows that the system can perform multiple extractions from complex physiological samples at reasonable throughput. The results also show that good sensitivity can be achieved as DA was readily detected at 3 nM (corresponding to 90 amol/sample).

The approach used here can be compared to other successful miniaturized systems for SPE-ESI-MS. In one report, droplet arrays were sampled into a low volume HPLC valve and then eluted through a capillary bed for ESI-MS. This approach uses low volume samples (100-600 nL); but, requires 100 nL of sample to inject 4 nL, a binary HPLC pump, and injection valve. Another approach is SPE on chip [N. Gasilova, L. Qiao, D. Momotenko, M. R. Pourhaghighi, H. H. Girault, Analytical Chemistry 85 (2013) 6254]. Without use of droplets these systems require relatively large volumes (over 1 □L) to extract and inject small volumes. They also require microfabrication. Thus, the approach provides a novel fluidic handling approach that uses low volume samples and simple instrumentation for SPE-ESI.

Example 2

All chemicals and reagents were purchased from Sigma-Aldrich (St. Louis, Mo.) unless otherwise specified. Leu-enkephalin (LE) was purchased from American Peptide (Sunnyvale, Calif.). HPLC grade water, methanol (MeOH) and acetonitrile (ACN) were from Burdick & Jackson (Muskegon, Mich.). Acetic acid was from Acros Organics (New Jersey). Fused silica capillary was from Polymicro Technologies (Phoenix, Ariz.). Artificial cerebral spinal fluid (aCSF) contained 145 mM NaCl, 2.68 mM KCl, 1.0 mM $MgSO_4.7H_2O$, 1.40 mM $CaCl_2$, 1.55 mM $Na_2HPO_4$, and 0.45 mM $NaH_2PO_4.H_2O$ adjusted to pH 7.4 (all salts purchased from Fisher Scientific, Pittsburgh, Pa.). LC-MS grade formic acid was purchased from Fisher Scientific (Pittsburgh, Pa.). Perfluorodecalin (PFD) was purchased from Acros Organics (New Jersey).

2.2 Sample Preparation and Analysis 2.2.1 Droplet Generation from a Multi-well Plate To perform SPE-ESI-MS, plugs of sample, rinse solvent, and elution solvent, all segmented by air or oil, were aspirated in the desired order into a 150 μm i.d.×360 μm o.d. high purity "plus" perfluoro alkoxy alkane (HPFA) tube (IDEX Health and Science, Oak Harbor, Wash.) as illustrated in FIG. 1A. Droplets were generated by sampling from a 384 multi-well plate (MWP) similar to previous reports [S. Sun, T. R. Slaney, R. T. Kennedy, Analytical Chemistry 84 (2012) 5794, J. Pei, Q. Li, M. S. Lee, G. A. Valaskovic, R. T. Kennedy, Analytical Chemistry 81 (2009) 6558]. The HPFA tubing was prefilled with PFD oil which yields reproducible droplet size (i.e., as opposed to filling an empty tube where air expansion tends to cause droplet size to vary). Pre-filling with PFD also leaves a coating on the wall and results in the aqueous droplets showing a convex meniscus (FIG. 2A), indicative of little wetting of the tubing walls and promoting low carryover. Samples were aspirated with a 100 μL Hamilton glass syringe (Fisher Scientific, Pittsburgh, Pa.) mounted on a PHD 200 programmable syringe pump (Harvard Apparatus, Holliston, Mass.). To generate segmented droplets, the inlet of the tubing was moved from well to well of the MWP by a computer-controlled XYZ-positioner while the syringe was operated in refill mode at 800 nL/min. The volume of the droplets and air or oil segments was controlled by the dwell time of the tubing inlet in or above the sample well.

For tests using LE as the analyte, the rinse droplet was 450 nL of 5% MeOH and 2% acetic acid, the elution droplet was 450 nL of 60% MeOH and 2% acetic acid, the sample droplet was 35 nL of 100 nM LE in aCSF and the blank droplet was aCSF. The air segments separating each of the aqueous droplets were ~15 nL (length=1 mm). For oil segmented droplets, 5-10 μL of PFD was placed on top of each well so that oil plugs were pulled into the tube after each sample or rinse plug. A small bubble of air was pulled into the tube as the tubing moved through the transition from well to well.

2.2.2 SPE-ESI-MS Analysis of Droplets

For SPE, a reversed-phase packed bed was prepared in-house using procedures similar those previously described [Y. Zhou, O. S. Mabrouk, R. T. Kennedy, Journal of the American Society for Mass Spectrometry 24 (2013) 1700]. Silica sol-gel frits were made in the outlet of a 75 μm i.d.×360 μm o.d. fused silica capillary. The column was packed to 2 mm total bed length using a slurry of 10 μm Altima C18 reversed phase particles (5 mg/mL particles in 75% acetone, Grace Davison, Deerfield, Ill.) at 200 psi. The net end of the capillary was cut to reduce the total capillary length to 2 cm. The outlet of the SPE packed bed was connected to a 75 μm i.d. Pt-coated fused silica electrospray emitter tip (FS-360-75-30-CE, New Objective, Woburn, Mass.). The emitter tip having a distal end and proximal end, with the proximal end having a tapered region in which the inside diameter and outside diameter reduces in size so that the inside diameter is typically 30 μm or smaller. The tubing containing the droplets was connected to the inlet end of the packed bed capillary. Connections were made by inserting the two capillaries into either end of a short length of polytetrafluoroethylene (PTFE) tubing (1/16" o.d., 0.010" i.d., Grace Davison, Deerfield, Ill.) that fit snugly over the capillaries so that the capillaries were butted against each other.

For analysis, droplets were pumped through the SPE packed bed at 500 nL/min (FIG. 1B) using a syringe pump (Fusion 400, Chemyx, Stafford, Tex.). The emitter tip was interfaced to a LCQ Deca XP Plus quadrupole ion trap MS (Thermo Fisher Scientific, Waltham, Mass.) operating in positive mode with a nanospray ionization source assembled in-house. LE was detected by $MS^3$ using the following m/z pathway: 556→397→278, 323, 380. The following MS parameters were used for detection of LE: automatic gain control (AGC) on, collisional induced dissociation (CID) q=0.25, isolation width m/z 3 (for parent and daughter ion) and m/z 1 (for granddaughter ions), collision gas=He, normalized collision energies=30%, activation time=0.25 ms, number of micro scans=1, maximum injection time=400 ms, spray voltage=+1.7 kV, capillary voltage=41 V and capillary temperature=100° C. Extracted ion currents (XICs) of assay components were used for analysis. Peak detection was performed using Xcalibur Qual Browser (Version 2.0, Thermo Electron Co.).

The sample cone of the MS was cleaned daily after use with 50% MeOH to prevent salt deposits from forming. After analyzing a series of samples, the SPE packed bed and emitter tip were flushed with 2% acetic acid in MeOH for 10 min and the rinse solvent for 10 min.

2.2.3 Dialysate Collection and MS Analysis

Microdialysis probes (1 mm dialyzing length) were implanted in the nucleus accumbens of male Sprague-Dawley rats weighing between 300-350 g under isoflurane anesthesia. The rats were then allowed to recover for 24 h prior to experiments. Microdialysis probes were perfused at 2 μL/min with a syringe pump for 1 h using a modified Ringer's solution (1.2 mM $CaCl_2$, 2.7 mM KCl, 148 mM NaCl and 0.85 mM $MgCl_2$). Flow rate was then reduced to 1 μL/min for 1 h prior to collections. The flow rate was then kept constant at 1 μL/min and samples were collected every 10 min. Samples were derivatized with benzoyl chloride as described elsewhere. The only modification to the derivatization procedure was to use carbonate buffer (100 mM $Na_2CO_3.H_2O$) in lieu of the borate buffer.

For analysis of dialysate, sample was added to a MWP and droplets were generated as described above. For dialysate assay, the rinse droplet was 10 mM ammonium formate and 0.15% formic acid, the elution droplet was 30:70 10 mM ammonium formate and 0.15% formic acid: ACN and 0.15% formic acid, the sample droplet was dialystate derivatized with benzoyl chloride (see conditions above) and the blank droplet was 250 μM ascorbic acid in aCSF. The droplets were infused into the same type of SPE packed bed and emitter tip as described above.

SPE-ESI-MS analysis of the dialysate droplets was performed as described above but using a triple quadrupole MS (TSQ Quantum, Thermo Fisher Scientific, Waltham, Mass.) for detection. The instrument was operated in multiple reaction monitoring mode for five analytes using the following m/z pathways: 251→105 for glutamine (Gln), 307→185 for glucose (Glc), 466→105 for dopamine (DA), 252→105 for glutamate (Glu) and 208→105 for γ-aminobutyric acid (GABA). For all dialysate experiments, the following MS conditions were used: spray voltage=2 kV, capillary temperature=100° C., collision gas=$N_2$, scan width m/z 2, scan time=0.150 s, collision energy=25 eV, number of microscans=1, Q1 peak width=0.70 and Q3 peak width=0.3. Extracted ion currents (XICs) of assay components were used for analysis. Peak detection was performed using Xcalibur Qual Browser (Version 2.0, Thermo Electron Co.).

3. Results and Discussion

Coalescence During Solid Phase Extraction-ESI-MS with Air segmented Droplets

To demonstrate utility of air-segmented gaps with coalescence, we performed SPE-ESI-MS on a series of samples using this approach. For all experiments, segmented arrays were created by aspirating a sequence of samples, air, rinse solvent, air, elution solvent, air, and re-equilibration solvent in the desired order and volume from a MWP, as depicted in FIG. 1. This array of plugs was driven by a syringe pump through an ESI emitter so that the samples were analyzed in series.

Analysis of Standards. For initial experiments we tested using air-segmented samples containing leu-enkephalin (LE). We chose 35 nL as a sample volume for these experiments to illustrate analysis at the nanoliter scale. The plugs were loaded into the tube such that during infusion, a sample droplet was first infused through the packed bed, retaining LE. Next, a rinse droplet containing 5% MeOH flushed the salts and other unretained chemicals from the packed bed. Then an elution droplet (containing 60% MeOH) eluted the retained LE. Finally another rinse droplet re-equilibrated the packed bed. Thus, the entire sequence of a normal SPE is encoded in the pre-formed droplet array so that the procedure can be performed without requirement of valves or binary or ternary solvent pumps.

Figure 1B:
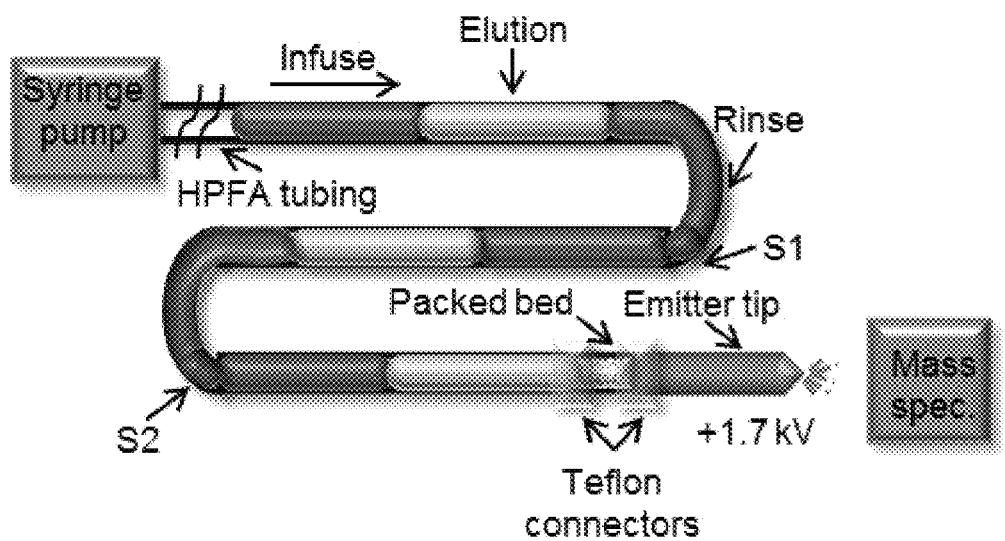

The array of plugs was pumped through an SPE bed and ESI nozzle for MS analysis (FIG. 1B). During infusion, the pressure needed to pump the droplets through the packed bed and emitter tip causes the air segments to compress resulting in coalescence of adjacent droplets (FIG. 2). Coalescence occurred even with longer air gaps (~1 cm). The mixing did not result is especially broad peaks as shown in FIG. 3A. This is likely because the gradient remains fairly sharp and reaches a concentration of organic solvent high enough to elute the test peptide over a short length of tubing.

As each elution plug emerged from the tip, a peak for LE was detected (FIG. 3A). Considering that LE could not be detected under these conditions without the SPE due to ion suppression, this result suggests effective desalting of the sample. The ability to detect different samples shows that coalescence did not result in merging of samples during extraction. For the sequence illustrated in FIG. 3A, blank samples containing aCSF but no LE were interspersed after every four samples. The blank droplets after each four LE samples show that carryover is 7±1% (n=4). Detection of 100 nM LE was reproducible with a peak area RSD of 11%. The variability may be due to inconsistency in sample generation, extraction efficiency or MS detection. Thus, results may improve with the use of an internal standard or refinement in plug generation.

The use of segmented flow allows calibration to be incorporated into a sequence. For example, FIG. 3B illustrates a trace from a series of droplets with LE concentration from 100 to 400 nM and the resulting calibration curve ($R^2 > 0.97$). Based on these data, the LOD was 10 nM, corresponding to 350 amol LE. The mass LOD is higher than we previously achieved for LE on this mass spectrometer (~1 amol) [34]; however, the goal of the experiments was not to test the limits of sensitivity and the instrument was not tuned for the peptide so considerable improvements may be attained by more care. As discussed below, better LODs can be obtained.

As shown by the traces in FIG. 3, pumping the sample array at 500 nL/min allowed generation of an SPE-ESI-MS analysis every 2.5 min. This throughput is reasonable and could be improved by use of higher flow rates; however, the flow rate in the present system was limited by the low pressure tolerance of connections used to join different pieces of tubing.

Analysis of real samples: brain dialysate. To illustrate the potential of segmented flow SPE-ESI-MS with coalescence for analysis of real samples, we used it to detect endogenous neurotransmitters and metabolites in dialysate collected from rat brain in vivo. The dialysate was benzoylated to enhance MS sensitivity and analyte retention on reversed phase columns as previously described [33]. Dialysate samples have a high concentration of inorganic salts and other compounds, which causes severe ion suppression effects in ESI-MS; therefore separation or extraction is required for analysis.

To test the suitability of segmented flow SPE-ESI-MS for analysis of dialysate, we prepared air-segmented aqueous droplets from dialysate fractions, elution, and rinse solvents as shown in FIG. 1. The rinse and elution solvents were modified to reflect the solvent strength of the typical LC gradient used to desalt the dialysate samples (see exact compositions in the Materials and Methods section). Infusing a series of samples with these conditions allowed extraction and simultaneous detection of five endogenous analytes (the neurotransmitters GABA, Glu, and DA and the metabolites Gln and Glc) in dialysate samples at 2.5 min intervals. FIG. 4 illustrates detection of a sequence of replicate droplets from a single dialysate sample. Overall the peak shape was satisfactory. DA elutes later than the other analytes and the peak is broader. DA is triply labeled with the benzoyl chloride moiety, making it very hydrophobic so it is highly retained on the reversed phase packed bed. As a result, the elution solvent used (70% ACN) may not be strong enough to elute DA as a sharp band. We also found that during a sequence of replicates, the peak area for later replicates could decrease (e.g., Gln and Glu in FIG. 5). Larger peak areas could be regenerated by rinsing the column with 100% ACN, suggesting that longer rinse cycles may be necessary for a large sample set of complex samples.

By comparing peak areas to a calibration curve we were able to estimate the concentration in dialysate as follows: GABA=55±15 nM, Gln=6.0±0.6 □M, Glu=580±104 nM, Glc=81±34 □M, and DA=2.7±0.2 nM (n=8 except for DA and Gln which had one point that was determined to be an outlier at 95% confidence by Grubb's test). All calibrations used 3 concentrations of analyte assayed in duplicate and had $R^2 > 0.99$. The determined concentrations are within expected values for dialysate under these conditions. The result shows that the system can perform multiple extractions from complex physiological samples at reasonable throughput. The results also show that good sensitivity can be achieved as DA was readily detected at 3 nM (corresponding to 90 amol/sample).

In microdialysis sampling, it is often of interest to collect smaller samples which correspond to better temporal resolution for monitoring rapid neurochemical events. It is also desirable to improve spatial resolution by using smaller probes; however, this also requires collecting smaller (e.g. nanoliter volume) samples. Collection, manipulation, and analysis of such small samples is challenging. Use of segmented flow provides a way of manipulating the nanoliter samples that are generated from small probes or at high temporal resolution [10-14]. In previous work, ICP-MS [23,24], capillary electrophoresis-laser induced fluorescence (CE-LIF) [12,13], enzyme assays [11,14] and direct ESI-MS [10] have been used to analyze segmented flow from in vivo sampling. The ability to use SPE-ESI-MS will undoubtedly allow more neurotransmitters and other endogenous analytes to be detected. For example, prior work has been unable to detect dopamine in segmented flow dialysate samples as we did here. Besides microdialysis samples, this approach may prove useful for other microscale samples such as single cells or blood spot punches.

Variations on this method. Droplet coalescence was generated in this case by using a SPE bed and ESI-emitter tip as flow restrictors which increased the back-pressure during flow. Other variations could be used. For example, only a SPE bed, a full-length chromatography bed, or only an ESI-emitter tip could be used. Segmented flow allows droplets to be segregated until the pressure is applied for flow. It is also possible to control the timing and spatial relationship of the droplet coalescence. In various embodiments, coalescence is controlled to occur inside the nanospray emitter, or external to (before) the emitter. For example in the case where the array is directly connected to the nanospray emitter (no SPE bed) coalescence can be controlled to occur inside the body of the emitter. Internal coalescence is enabled by connecting the air-gapped, segmented flow array to an "empty" (air-filled, rather than liquid filled) nanospray emitter, fabricated from tubing having the same, or larger, inside diameter as the array. When the pump pressure is first applied, the array, or some portion of it, will transfer into the nanospray emitter as an intact segment array. This happens because the air-filled emitter does not generate a sufficient back-pressure to enable coalescence until the first liquid segment of the segment array fills the tapered region of the nanospray emitter. When the first liquid segment fills the tapered region, the pressure inside the conduit increases, and provided pump pressure, compression of the air gaps will occur inside the emitter tip with subsequent droplet coalescence. In other embodiments, droplet coalescence is made to occur before the segment array enters the emitter body. This is enabled by connecting the array to an emitter that is pre-filled with liquid mobile phase and/or an emitter that is fabricated from tubing having an internal diameter that is sufficiently small to generate back pressure suitably high to force coalescence. Such emitters are commonly fabricated from 20 μm ID tubing, and tapered to a 10 μm ID nozzle at the proximal end.

Gradient Elution LC

The observation of a merged droplet under pressure (FIG. 2B) and utility as a step gradient (i.e., sudden rise in solvent strength) for SPE, suggests the possibility of performing gradient elution liquid chromatography using this approach. Typical gradient elution LC is performed using gradient pumps that create changes in mobile phase composition over time for high-pressure LC (HPLC) or ultra-high pressure LC (UHPLC). Forming such gradients is challenging. Indeed, the most expensive part of an HPLC system is the typically the pump. The challenges are even greater for small-bore columns because of the low-volumes (e.g., packed capillary, open tubular, or nanoLC).

According to the current teachings, use of segmented flow with droplet coalescence allows gradients to be pre-formed, stored, and then used for separation. In various embodiments, an array of droplets of increasing solvent strength is made as shown in FIGS. 5A and 5B. The sample can be aspirated as the last step. The entire tube can then be pressurized and pumped through the LC column using a simple pump that only drives a single solvent thus eliminating the need for injection valves and gradient pumps. The droplet content, composition, and size are manipulated during aspiration to form the desired gradients. Pumping this droplet array through the tube compresses the droplets and allows gradient elution LC at the nanoliter scale, with no solvent split or expensive gradient pumps.

Oil Segmented Droplets

To further enhance the utility of droplet coalescence, incompressible and immiscible "spacer" droplets of oil, such as perfluorodecalin, are interspersed to prevent coalescence among some adjacent droplets. In such a way, arbitrary arrays of droplets or segments that merge and do not merge could be created. In this way certain droplets are mixed or combined, e.g. to initiate reactions or create elution gradients, while other droplets, e.g. other samples, are kept separate. FIGS. 6A and 6B illustrate arbitrary arrangements of oil and air-segmented liquid phase droplets that are coalesced after pressurization. FIG. 7A illustrates how a bubble between two oil-droplets can be compressed but the oil keeps adjacent samples separate under pressure.

To illustrate, this approach was used to perform a series of SPE-ESI-MS analyses. Droplet arrays of sample, oil, air, oil, rinse, oil, air, oil, elution, oil, air, oil, re-equilibration were created and pumped through an ESI emitter with SPE bed. Using such segments, we were able to perform a series of SPE-ESI-MS assays for LE in aCSF (FIG. 7B) with low carryover (0.4%) at 2 min intervals. The improved carryover relative to the air segmented samples may be due to prevention of droplet coalescence during infusion. The reproducibility of the peak areas for these segments was slightly worse than for air segmented droplets (14% and 11% respectively); but this difference was not statistically significant ($F_{(7,11)}=1.7$, $p>0.05$). These results illustrate that the oil segmented samples can also be used for SPE-ESI-MS.

The ability to keep the samples completely separate appears to lower carry-over. It could also enable higher throughput by allowing higher flow rates and larger number of samples to be analyzed from one tube. However, realizing these advantages will require use of higher pressure fittings to connect the tubing to the packed bed and emitter tip.

Other applications. In various embodiments, the flow restrictor and coalescence are used to initiate reactions in adjacent droplets or to dilute droplets. Particularly important are classes of chemical reactions that include those enabling the highly specific detection of analytes through instrumental analysis including, but not limited to: spectroscopic means such as absorption, luminescence, or fluorescence; electrochemical methods; radiochemical methods; and ionization and detection by various forms of mass spectrometry.

The spatial control of coalescence for example plays a role in the use of chemiluminescence for detection. In an illustrative embodiment, a reagent droplet (containing the reactive luminescent compound) is coalesced with an analyte-containing droplet immediately prior to optical detection of light from the chemical reaction. As soon as the two droplets coalesce, the chemical reaction will initiate and light will be emitted from the mixed droplet The detection of emitted radiation is (1) in close proximity to the optical sensor and (2) proximate in time as chemiluminescence exhibits a kinetically controlled response with the decay of emitted light radiation occurring with (potentially exponential) decay in relation to analyte concentration.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method comprising
providing a one-dimensional linear array of liquid plugs in a conduit, said conduit having a continuous, closed-form inner surface having an opening at the proximal and distal ends of the conduit and furthermore containing a restriction comprising a solid phase porous substrate, located at the distal end of the conduit, wherein the array comprises two adjacent liquid plugs separated by a gas phase;
applying a pressure to the proximal end of the conduit advancing the linear array along a flow path toward the restriction;
applying sufficient pressure to the proximal end of the conduit to cause the two adjacent plugs and the gas phase separating them to coalesce into a single plug; and
advancing the coalesced single plug through the restriction.

2. The method of claim 1, wherein the solid phase porous substrate comprises a packed particle bed, a porous phase coated on the interior walls of the conduit, or a porous monolith.

3. The method of claim 1, wherein the restriction comprises a liquid chromatography column or a solid phase extraction bed.

4. The method of claim 1, wherein the adjacent liquid plugs are solutions having different concentrations of solute, and the resulting coalesced plug comprises a concentration gradient of the solute along the length of the conduit.

5. The method of claim 1, wherein the conduit contains a plurality of arrays, and the arrays in the conduit are separated by spacer plugs, wherein the spacer plugs comprise a liquid immiscible with a solvent found in the liquid plugs of the array.

6. The method of claim 4, wherein the adjacent fluid plugs comprise water, a water soluble organic solvent, or a combination.

7. The method of claim 5, wherein the spacer plugs comprise a perfluorocarbon liquid.

8. The method of claim 1, wherein the adjacent fluid plugs comprise reagents that react with one another when the plugs are coalesced.

9. The method of claim 1, wherein at least one of the adjacent fluid plugs comprises a solute that is diluted when the adjacent plugs coalesce.

10. The method of claim 1, wherein the array comprises more than two liquid plugs.

11. A method, comprising:
forming a one dimensional linear array in a conduit by aspirating a plurality of liquids in a desired order into a tube having a diameter sized such that the aspirated liquids form plugs that span the inner diameter of the tube, wherein the plugs are separated from one another by a gas phase plug aspirated between the aspirated liquids;
applying pressure to the linear array to coalesce at least two adjacent plugs and the gas phase separating them in the conduit; and
advancing the coalesced plugs to pass through a separation device.

12. The method of claim 11, wherein the separation device is a chromatography column or a solid phase extraction bed.

13. The method of claim 12, wherein the output of the separation device is provided to an electrospray ionization emitter nozzle.

14. The method of claim 11, wherein the aspirating is performed with a first pump and the advancing is performed with a second pump.

15. The method of claim 14, wherein the first pump and the second pump are not the same.

16. The method of claim 11, wherein the linear array comprises a plurality of plugs comprising different levels of the same solute, and wherein the plurality of plugs is coalesced into a single plug having a gradient of solute concentration when the pressure is applied to the linear array.

17. The method according to claim 11: wherein the plugs in the linear array comprise, in order, a sample droplet, a rinse droplet, an elution droplet, and a second rinse droplet; wherein applying pressure to the linear array coalesces the droplets and the gas phases separating them; and wherein the sample droplet is one that deposits the sample on the substrate, the rinse droplet is one that washes unretained components out of the substrate, the elution droplet is one that elutes the sample from the substrate, and the second rinse droplet is one that reconditions a solid phase porous substrate of the separation device.

18. The method of claim 17, wherein the sample droplet comprises a fluid sample of biological origin.

19. The method of claim 17, further comprising providing the output of the solid phase porous substrate to a mass spectrometer.

20. The method of claim 17, wherein the solid phase porous substrate comprises a packed bed of silica particles.

* * * * *